March 13, 1973 O. RIEGER Plant Pat. 3,318
BEGONIA PLANT
Filed June 30, 1971
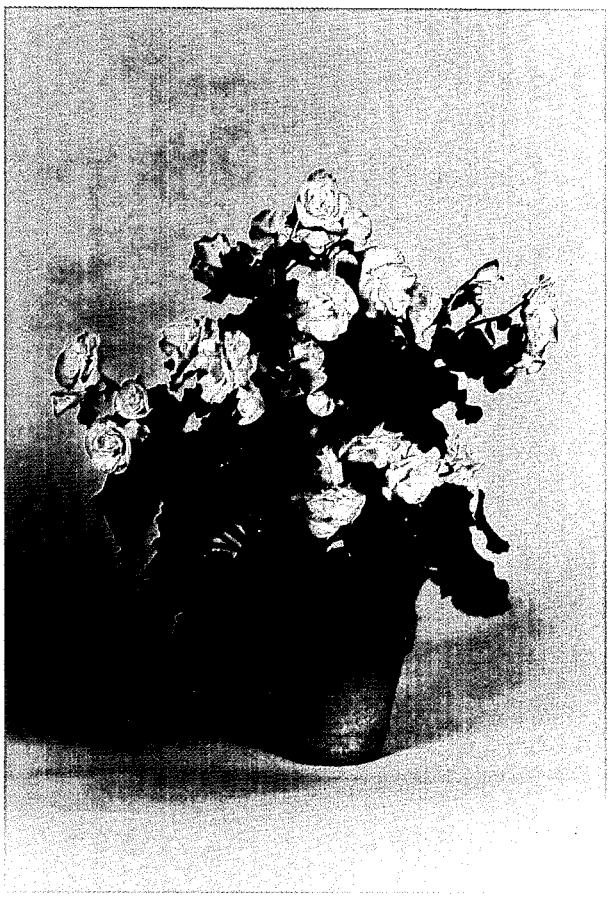

United States Patent Office

Plant Pat. 3,318
Patented Mar. 13, 1973

3,318
BEGONIA PLANT

Otto Rieger, deceased, by Gertrud Rieger, legal representative, Nurtingen, Germany, assignor to Mikkelsens, Inc., Ashtabula, Ohio Filed June 30, 1971, Ser. No. 158,642
Int. Cl. A01h 5/00
U.S. Cl. Plt.—68 1 Claim The present invention relates to a new and distinctive variety of begonia plant botanically known as *Begonia elatior* discovered by me as a color mutation of an unpatented but commercially well-known begonia hybrid known as Rieger's Aphrodite.

The new mutation was discovered in nurseries in Nurtingen, Germany, and when asexually reproduced by cuttings at Nurtingen, Germany, has been found to retain its unique characteristics through successive propagations.

The distinguishing feature of the new variety when compared with the parent variety is the light pink petal color of the double azalea like flowers, compared to the light rose red petal color of the parent variety.

The following characteristics distinguish the new variety and its parent from other commercial begonia varieties of this type:

(1) Flowers are quite numerous and borne on trusses that need support unless they are used for cascading or trailing displays.

(2) Flowers are double azalea type possessing very few, if any, reproductive parts.

(3) Flowers are very durable and long lasting, with continuous flowering in the summer period for three to four months.

(4) Propagation is mostly by top cuttings as leaf cuttings seldom produce underground shoots.

(5) Overall plant growth is compact. Self-branching is prominent giving full body to the terminal areas of the plant.

(6) Overall growth is somewhat soft under poor light condition, necessitating some support by staking since there is very little development of underground shoots to give fullness in the lower areas of the main plant trunk.

(7) Foliage is dark green with a resilient texture that is tolerable to injuries that normally occur in handling. The foliage is relatively resistant to the common foliar disorders of begonias, especially mildew and botrytus.

(8) The soft type growth that occurs during the spring months or in periods of restricted sunlight allows this begonia variety to be grown as a cascading or hanging basket type developing trailing trusses of flowers several feet in length in a short period of time. This is of significant economic importance in begonia culture.

The accompanying colored photograph illustrates the flowering of a supported plant and shows typical foliage and overall growth of this new begonia as it is reasonably possible to reproduce in color for such purposes.

The following detailed description of my new begonia variety is based on observations on the new variety grown under commercial methods in Nurtingen, Germany. Color references are to the Royal Horticultural Society Colour Chart, except where general color terms of ordinary dictionary significance are used.

Propagation: Terminal cuttings and stem bud cuttings root in approximately three weeks time using 20° C. temperature in the propagation media. Leaf cuttings are not utilized as they do not regenerate bottom shoots readily.

Rooting habit: Roots are abundant, fine textured and respond rapidly in loose, well aerated composts.

Plant form: Plants are semidwarf, generally compact and full as a result of free self branching characteristics. Leaf internodes are close. Overall growth is somewhat less rapid than the parent variety.

Habit of growth: Vigorous and upright under good natural light conditions. Plants need support during poor light periods of the year. The variety can be cultivated for a trailing or cascading type during the periods of low light intensity because of its soft flexible character under such conditions.

Blooming habits: Flowering is initiated during short days and 18° C. temperature. Both the new variety and its parent flower continuously during the summer similarly to *Begonia semperflorens*.

Blooming season: Under appropriate greenhouse cultural techniques, this variety can be brought into flower any season of the year. It is best adapted for late spring, summer, and early fall seasons.

Foliage: Alternate: borne at close angle to the stem, being average to above average in quantity. Foliage feels somewhat waxy or greasy and is relatively resilient to normal handling.

(*a*) *Size.*—Medium for commercial begonias at maturity, being approximately 6 to 10 cm. long by 4 to 8 cm. wide. Environmental and general plant conditions can greatly alter the size and color of the foliage.

(*b*) *Shape.*—Oval pointed, heart shaped.

(*c*) *Texture.*—Upper side—smooth; leathery; waxy or greasy to the feel, but somewhat flat in appearance. Under side—smooth, glossy, highly reflective.

(*d*) *Margin.*—Slightly indented and serrated in young foliage. Leaf edges become smooth in older mature foliage with some wavy effect. Lobes at petiole are usually unbalanced in size.

(*e*) *Color.*—New foliage—upper side near RHS 143 A; under side near RHS 146 C. Old foliage—upper side near RHS 136 A; under side near RHS 148 B with some tendency to have red pigmentation infusion.

Disease resistance: The foliage is quite resistant to both mildew and botrytus as tested with susceptible begonia varieties under normal cultural conditions of the greenhouse.

Flowers: Double azalea type that show very few if any reproductive parts.

(*a*) *Borne.*—On trusses with multiple clusters. If trusses are trained for trailing or cascading hanging basket types, the flower truss can develop under optimum conditions to several feet in length in a relatively short period of time. The extreme long lasting quality of the individual blooms is a beneficial character for this type of specimen. Bloom size depends on the number of blooms produced per plant, but blooms often measure 4 to 6 cm. across.

(*b*) *Quantity.*—Extremely floriferous, unusually long lasting, and continuous flowering over a relatively long period of time.

(*c*) *Petals.*—Color—nearly RHS 52 B or C.

(*d*) *Buds.*—Develop progressively at the nodes to the size and shape of a lima bean, approximately 2 cm. in diameter before opening. The lighter reverse coloring can be seen before opening.

(*e*) There are insufficient reproductive parts to be described.

I claim:

1. A new and distinct variety of begonia which is distinguished from the parent variety Rieger's Aphrodite by its light pink petal color and which, together with the parent variety Rieger's Aphrodite, distinguishes from other commercially available begonia varieties of this type by its numerous double azalea type flowers which are durable and long lasting, are borne, on trusses and which have few, if any, reproductive parts, its compact growth and self-branching habit, its dark green, resilient foliage which is relatively tolerant to handling and relatively resistant to disease, and by its soft type growth habit in spring months or in periods of restricted sunlight which allows the new variety to be cascaded or trailed.

No references cited.

ROBERT E. BAGWILL, Primary Examiner